(12) United States Patent
Richards

(10) Patent No.: US 7,115,145 B2
(45) Date of Patent: Oct. 3, 2006

(54) ACETABULAR COMPONENT

(75) Inventor: Mark Isom Richards, Leander, TX (US)

(73) Assignee: Zimmer, Inc., Chicago, IL (US)

( * ) Notice: Subject to any disclaimer, the term of this patent is extended or adjusted under 35 U.S.C. 154(b) by 409 days.

(21) Appl. No.: 10/613,157

(22) Filed: Jul. 3, 2003

(65) Prior Publication Data

US 2005/0004678 A1    Jan. 6, 2005

(51) Int. Cl.
*A61F 2/32*    (2006.01)
*A61F 2/30*    (2006.01)

(52) U.S. Cl. ............... 623/22.29; 623/22.2; 623/22.28; 623/18.11

(58) Field of Classification Search ............... 623/22.2, 623/22.29, 22.24, 22.15, 22.17, 22.19, 22.28
See application file for complete search history.

(56) References Cited

U.S. PATENT DOCUMENTS

| | | | |
|---|---|---|---|
| 4,642,123 A | 2/1987 | Noiles | |
| 4,795,471 A * | 1/1989 | Oh | 623/22.19 |
| 5,263,988 A | 11/1993 | Huebner | |
| 5,425,778 A * | 6/1995 | Zichner et al. | 623/22.29 |
| 5,667,508 A * | 9/1997 | Errico et al. | 606/73 |
| 2003/0050703 A1* | 3/2003 | Harris et al. | 623/22.2 |

FOREIGN PATENT DOCUMENTS

GB    2116847    10/1983

\* cited by examiner

*Primary Examiner*—Pedro Philogene
(74) *Attorney, Agent, or Firm*—Williams, Morgan & Amerson, P.C.

(57) ABSTRACT

An acetabular prosthesis generally consists of an acetabular component and an acetabular shell. The acetabular component includes an acetabular articulating component and an acetabular constraining component. The articulating component has a hemispherical or dome shape that defines a hemispherical cavity for receiving a femoral ball of a femoral hip stem. The constraining component has a ring-shape body with extensions for locking the femoral ball in the cavity of the articulating component.

20 Claims, 5 Drawing Sheets

ACETABULAR COMPONENT

FIELD OF THE INVENTION

The invention relates to an acetabular prosthesis and, more particularly, to a prosthetic acetabulum for a hip joint.

BACKGROUND

Acetabular prostheses generally consist of two separate components, an acetabular shell or cup and an acetabular insert or liner. The shell has a hemispherical shape and is affixed and embedded into a cavity formed in a natural acetabulum of a patient. The insert has a hemispherical shape to mate with an internal cavity of the shell. A low friction bearing surface is formed along a spherical cavity in the insert and is adapted to articulate with a femoral ball of a hip stem.

The shell is made of a biocompatible metal or metal alloy, and the insert is made of a polymer, such as ultrahigh molecular weight polyethylene. Regardless of the materials or geometries, these two components are generally locked together with the shell encompassing the external surface of the insert Once the shell is embedded in bone of the natural acetabulum and the insert has been assembled within the shell, the insert is ready to receive the femoral ball.

Hip prostheses can experience impingement, subluxation, and even dislocation after being implanted in the patient. For instance, the spherical femoral ball of the hip stem can become dislocated from the acetabular component. This dislocation can occur from various reasons, such as trauma to the leg or abnormal twisting of the leg. In some instances, an additional surgical procedure is required to remedy dislocation of a prosthetic hip.

Due to the occurrence of impingement, subluxation, and other problems, it is desirable to have an acetabular insert that inhibits subluxation and dislocation of the femoral ball from the socket. In some designs, the insert is configured to have more than a hemispherical shape. In other words, the insert encloses and captures more than half of the femoral ball within the spherically shaped cavity of the insert itself. In some instances, a locking ring is used to lock the femoral ball into the cavity of the acetabular liner. Prior patents illustrate an effort to design an insert with a spherically shaped cavity to capture the femoral ball using a locking ring.

U.S. Pat. No. 4,642,123 entitled "Ball and Joint Socket Bearing for Artificial Joint" to Noiles teaches, in one embodiment, an acetabular shell having two coaxial pin members and an acetabular liner having more than a hemisphere in one plane. The liner is rotatable within a spherical cavity of the shell about the coaxial pin members. In other embodiments, a retaining ring is used in conjunction with the shell and liner.

U.S. Pat. No. 5,002,577 entitled "Variable Position Acetabular Cup" to Bolesky et al. teaches an acetabular prosthesis having a shell, a liner, and an adaptor ring. The shell and liner have a symmetrical shape while the adaptor ring has a non-symmetrical shape. This adaptor can be mounted on the shell in a plurality of positions to change the position of the symmetrical liner after the shell is secured in the acetabulum.

U.S. Pat. No. 5,800,555 entitled "Acetabular Cup Bearing Liner" to Gray teaches a bearing liner formed with a rim that defines an opening to a concave bearing surface that encompasses more than a hemisphere. A channel is formed at the opening of the cavity to permit elastic deformation of the liner to allow the femoral ball to pass into the cavity. A locking component engages the liner to inhibit elastic deformation and capture the femoral ball.

U.S. patent application publication 2003/0050703 A1 entitled "Acetabular Components That Decrease Risks of Dislocation" to Harris et al. teaches an acetabular assembly having a metal shell, a monopolar acetabular liner, and a constraining ring. The constraining ring is circular in shape and has cutouts similar to that of the liner.

It, therefore, would be advantageous to provide an acetabular prosthesis that provides an increased range of motion with respect to the femoral ball and reduces the occurrence of impingement, subluxation, and dislocation of the femoral ball from the acetabular insert.

SUMMARY

The present invention relates to an acetabular prosthesis and, more particularly, to a prosthetic acetabular component for a hip joint. In one embodiment, the acetabular component is adapted to be connected with an acetabular shell to form an acetabular prosthesis. This prosthesis is inserted into a bone cavity of the natural acetabulum.

In one embodiment, the acetabular component generally consists of an acetabular articulating component and an acetabular constraining component. The articulating component generally has a spherical or dome shape extending between outer and inner surfaces that define a hemispherical cavity for receiving a femoral ball of a femoral hip stem. The outer surface has a convex shape and may be adapted to engage an inner surface of an acetabular shell. The inner surface has a concave shape with a smooth articulating surface adapted to articulate with the femoral ball. A base portion provides an entrance way or opening into the cavity of the articulating component This base portion includes two extensions or tabs that extend outwardly from a rim. Two cutouts or recesses are positioned between the extensions.

The constraining component is adapted to constrain or lock the femoral ball within the cavity of the articulating component. The constraining component has a body with a ring shape. Two extensions or tabs extend outwardly from the body, and two cutouts are positioned between the two extensions. When the constraining component is attached to the articulating component, the extensions and cutouts on each component generally align.

The constraining component is adapted to engage and connect or lock with the articulating component. In one embodiment, while the femoral ball is positioned in the cavity of the articulating component, the ring portion of the body of the constraining component is positioned around the base portion of the articulating component. Simultaneously, the cutouts and extensions on the constraining component align with the cutouts and extensions on the articulating component. In this position, the constraining component prevents the extensions on the articulating component from radially expanding. As such, the femoral ball is trapped or constrained in the cavity of the articulating component.

As one feature, the constraining component captures and constrains the femoral ball while simultaneously providing the hip stem with a wide range of motion. The extensions of the constraining and articulating components do not fully extend circumferentially around the base portion of the articulating component. During range of motion of the femoral hip stem, a neck or body of the stem will occupy the area of the cutouts rather than impinging against the extensions. The constraining component is attached to the articulating component to constrain the femoral ball yet not impede its range of motion.

DETAILED DESCRIPTION

Figure 1:
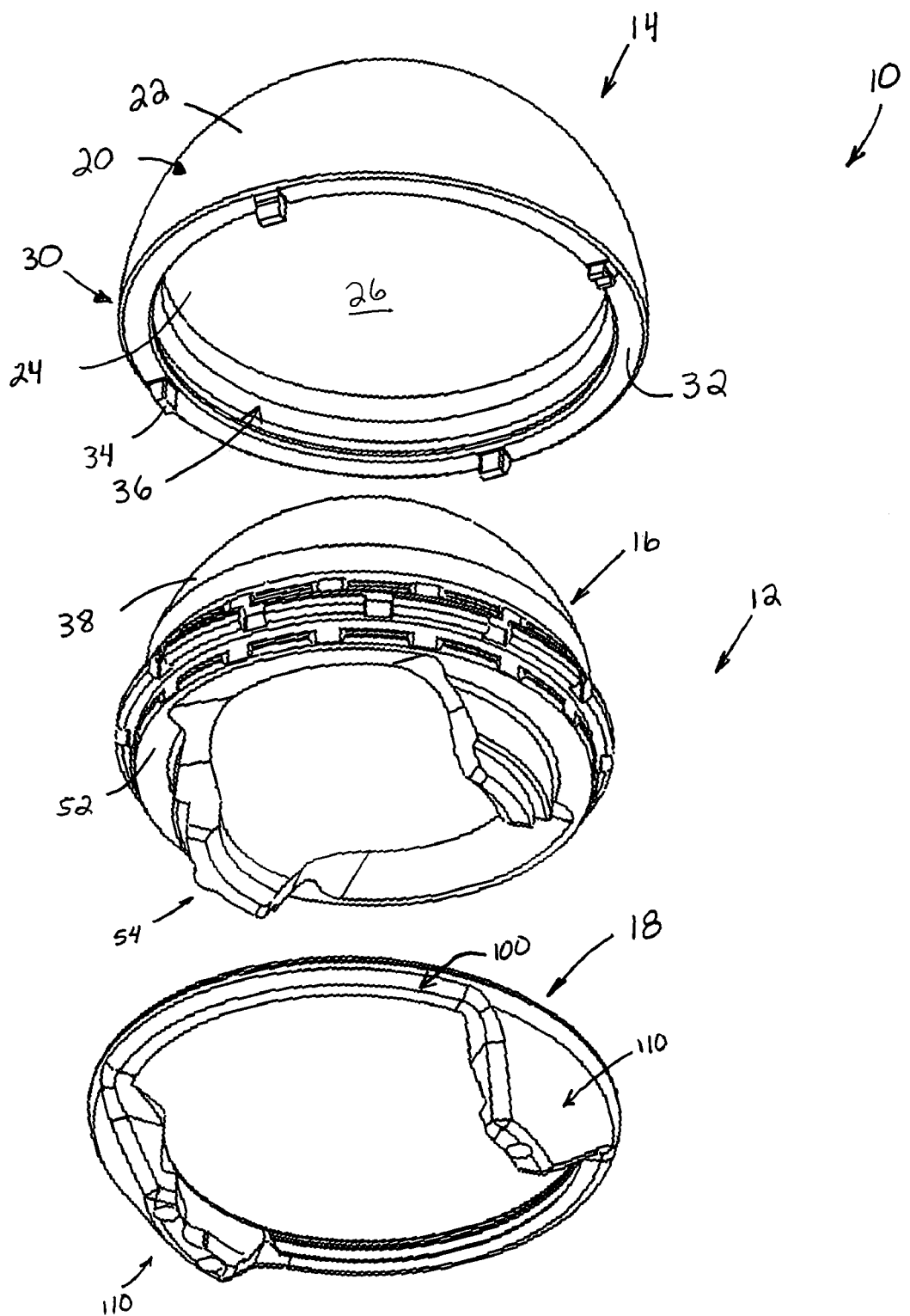
FIG. 1 is an exploded view of the acetabular component and acetabular shell of one embodiment of the present invention.
Figure 2:
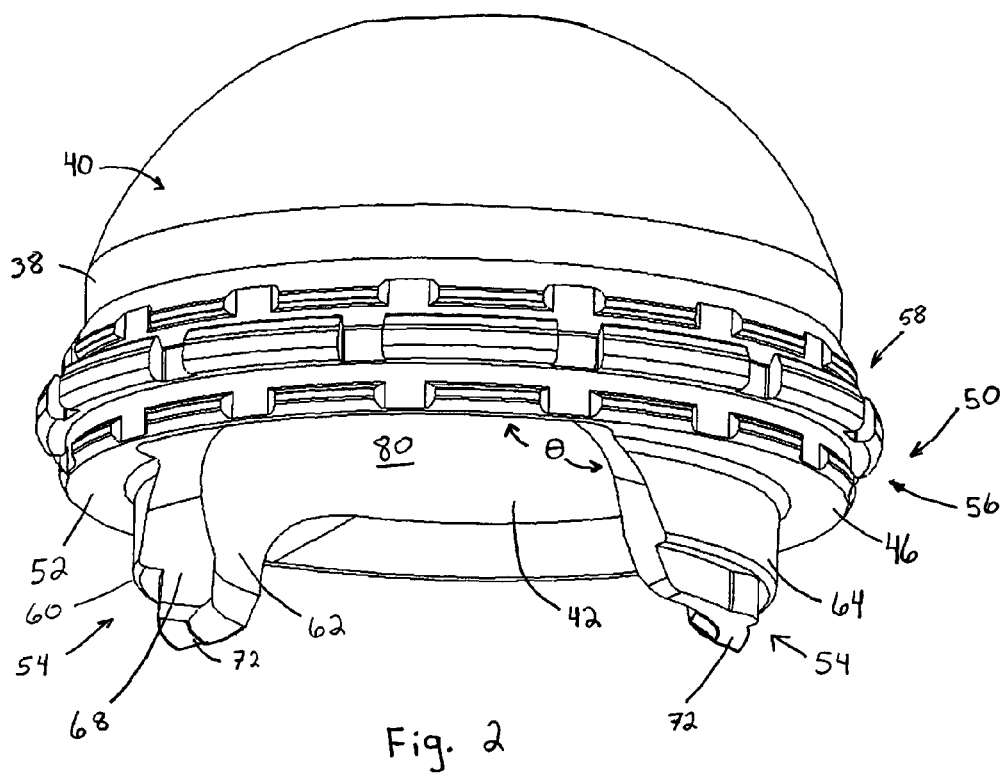
FIG. 2 is a side perspective view of the articulating component of FIG. 1.
Figure 3:
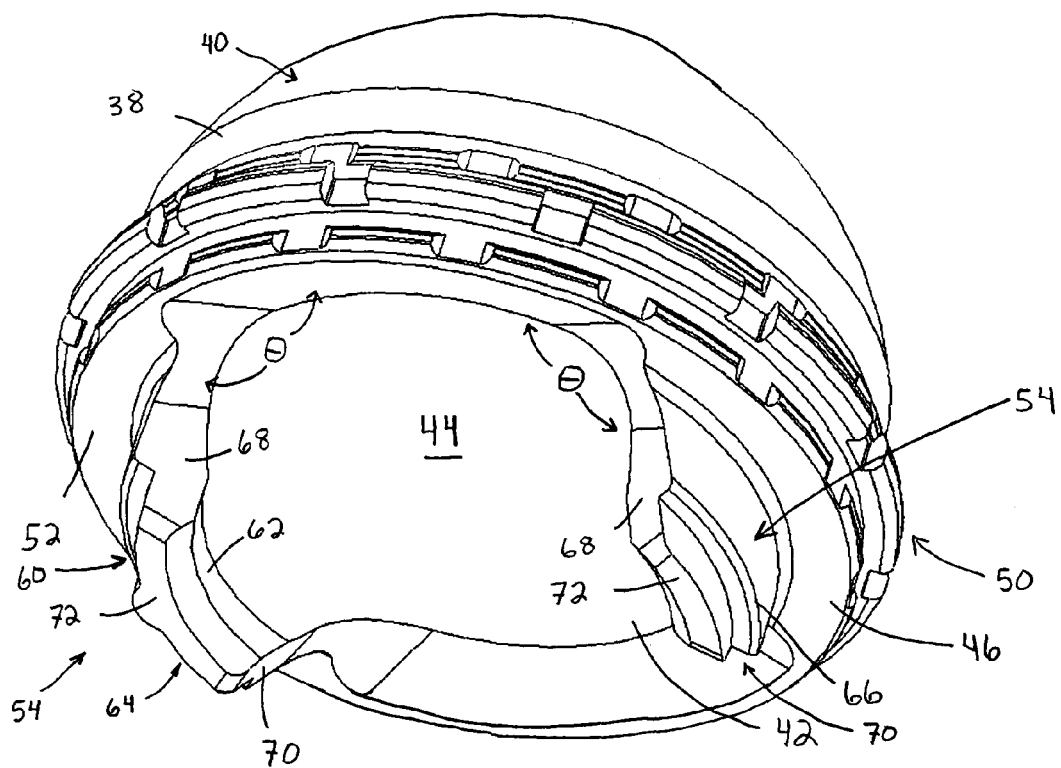
FIG. 3 is another perspective view of the articulating component of FIG. 1.

FIG. 1 shows an exemplary embodiment wherein an acetabular prosthesis 10 generally consists of an acetabular component 12 and an acetabular shell 14. Acetabular component 12 includes an acetabular articulating component 16 and an acetabular constraining component 18.

Acetabular component 12 can be used as an acetabular insert that connects with a separate acetabular shell (as illustrated in FIG. 1) or without the shell 14 and adapted to function simultaneously as both a shell and insert. In this latter configuration, the acetabular component 12 is directly inserted into a natural acetabulum of a patient; a separate shell is not required.

Shell 14 generally has a hemispherical or dome shaped body 20 with an outer surface 22 and inner surface 24. The inner surface 24 defines a hemispherical cavity 26 for receiving an outer surface of the articulating component 16. Outer surface 22 has a hemispherical or dome shape that may be adapted to engage and attach or integrate with natural bone of an acetabulum of a patient. An annular base portion 30 extends around the shell. This base portion includes a distal end with an annular platform or ring-shaped surface 32 that provides an entrance way or opening into the cavity 26. A plurality of tabs 34 extend downwardly from surface 32. Further, base portion 30 along inner surface 24 includes a locking mechanism 36 adapted to engage and lock with articulating component 16.

Looking to FIGS. 1-4, articulating component 16 generally has a partial spherical or dome shaped body 38 with an outer surface 40 and inner surface 42. The inner surface 42 defines a partial spherical or hemispherical cavity 44 for receiving a femoral ball of a femoral hip stem. Inner surface 42 has a concave shape with a smooth articulating wall or surface adapted to articulate with the femoral ball. The outer surface 40 has a hemispherical or dome shape with a surface that is adapted to engage inner surface 24 of acetabular shell 14. An annular rim 46 extends around an outer perimeter of the articulating component along a base portion 50. This base portion includes a distal end with an annular platform or ring-shaped surface 52 that provides an entrance way or opening into the cavity 44 of the articulating component 16.

Two extensions or tabs 54 extend outwardly from surface 52. Preferably, these extensions are oppositely disposed from one another.

A first set of notches or recesses 56 is evenly spaced circumferentially around an outer edge of base portion 50. A second set of notches or recesses 58 is evenly spaced circumferentially around the outer surface and above notches 56. Notches 58 are adapted to engage and lock with the locking mechanism 36 of shell 14. Both sets of notches have polygonal shapes, but these notches can have various shapes and sizes known in the art. U.S. Pat. No. 6,129,765 entitled "Locking Mechanism for Acetabular Cup" to Lopez et al. teaches a locking mechanism for an acetabular cup and is fully incorporated herein by reference.

Extensions 54 have a body 60 with an inner wall 62 and an outer wall 64. Both walls circumferentially extend around a portion of surface 32. Wall 62 has a smooth surface with a spherical contour. Wall 64 has a step or terrace 66 that extends along the length of wall 64 from a first end surface 68 to a second end surface 70. In the exemplary embodiment, end surfaces 68 and 70 are not perpendicular with surface 52. Instead, surface 68 and 70 form an obtuse angle θ with surface 52. These surfaces 68 and 70 thus taper or slope inwardly from surface 52 to a top surface 72. Preferably, the taper on these surfaces is constant, gradual, and symmetric with respect to each other. Further, in the exemplary embodiment, the extensions are similarly shaped but may be formed with different sizes. For example, one extension may be larger than the other. Alternatively, the extensions can have the same size.

As shown, extensions 54 do not completely circumferentially extend along surface 52. Two gaps or cutouts 80 are formed between extensions 54. These cutouts are oppositely disposed from each other.

Figure 4:
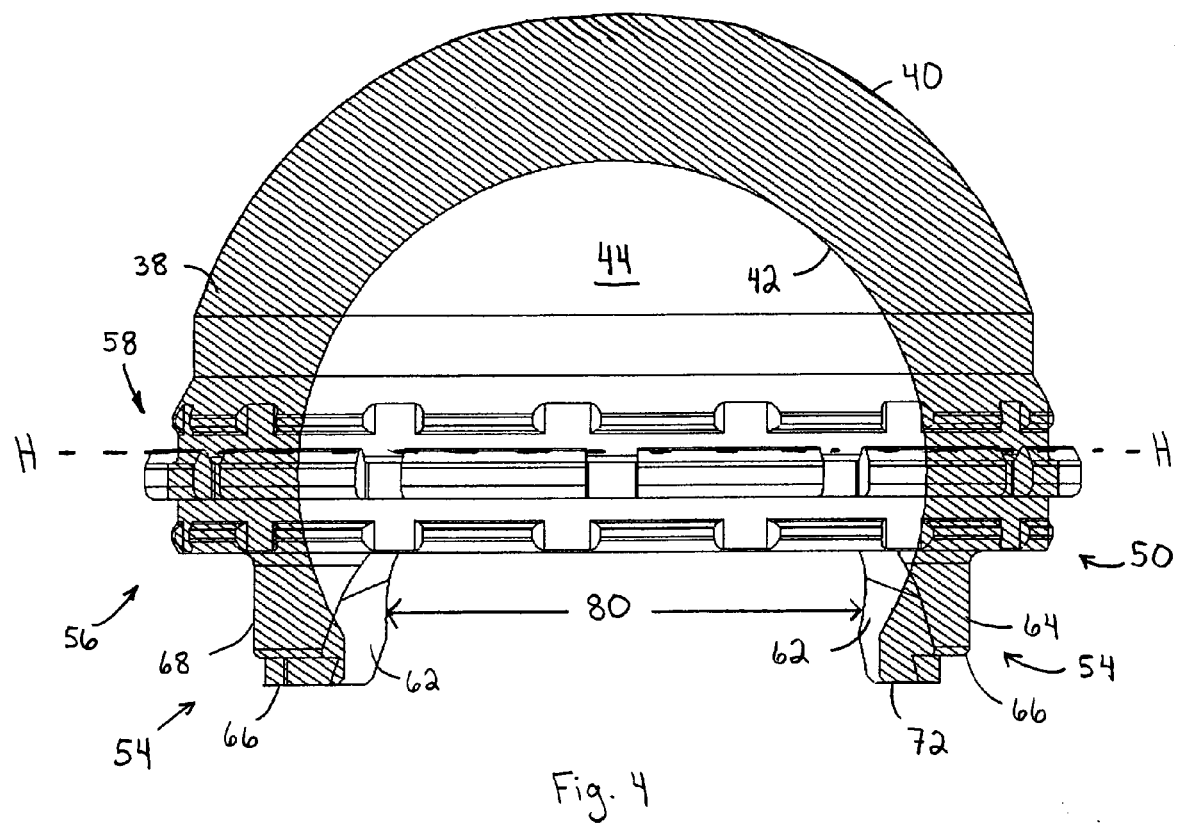
FIG. 4 is a cross-sectional type view of the articulating component of FIG. 1.

As best shown in FIG. 4, articulating component 16 has a spherical configuration. Dashed line H—H approximates the hemispherical line through the articulating component. As shown, extensions 54 extend downwardly below the hemispherical line H—H to provide articulating component with a body having more than a hemisphere. Inner walls 62 of extensions 54 form a partial spherical surface that provides a continuous spherical extension below surface 52 and below line H—H. These extensions extend below line H—H to capture and retain the femoral ball of a femoral hip stem.

Figure 5:
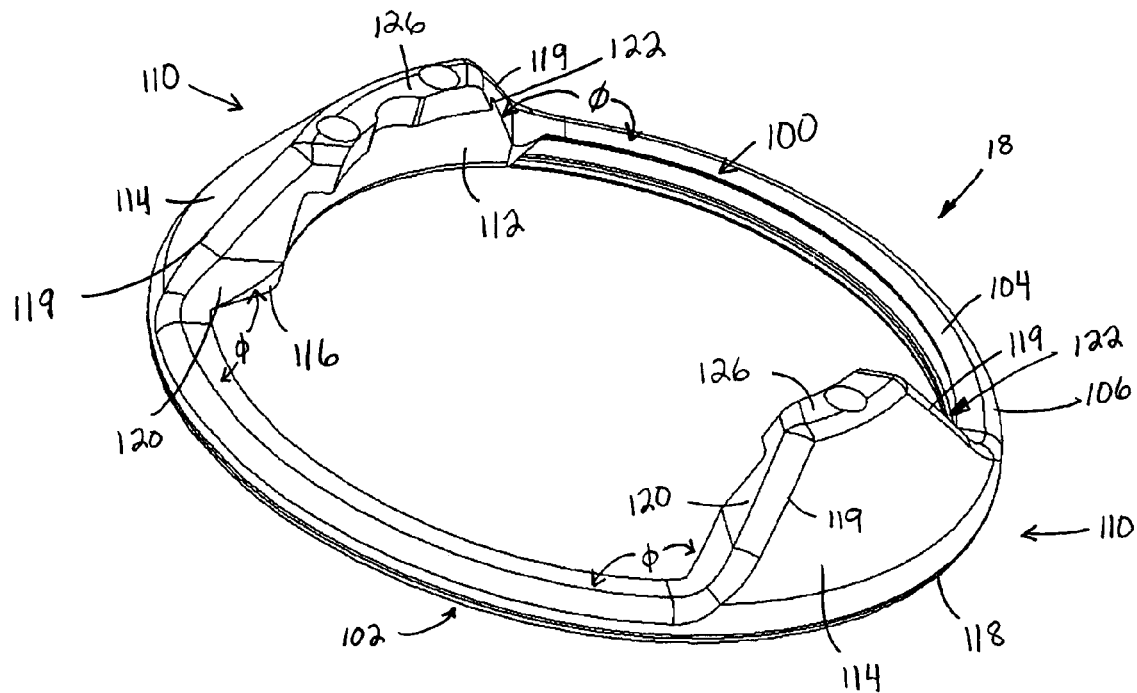
FIG. 5 is a perspective view of the constraining component of FIG. 1.
Figure 6:
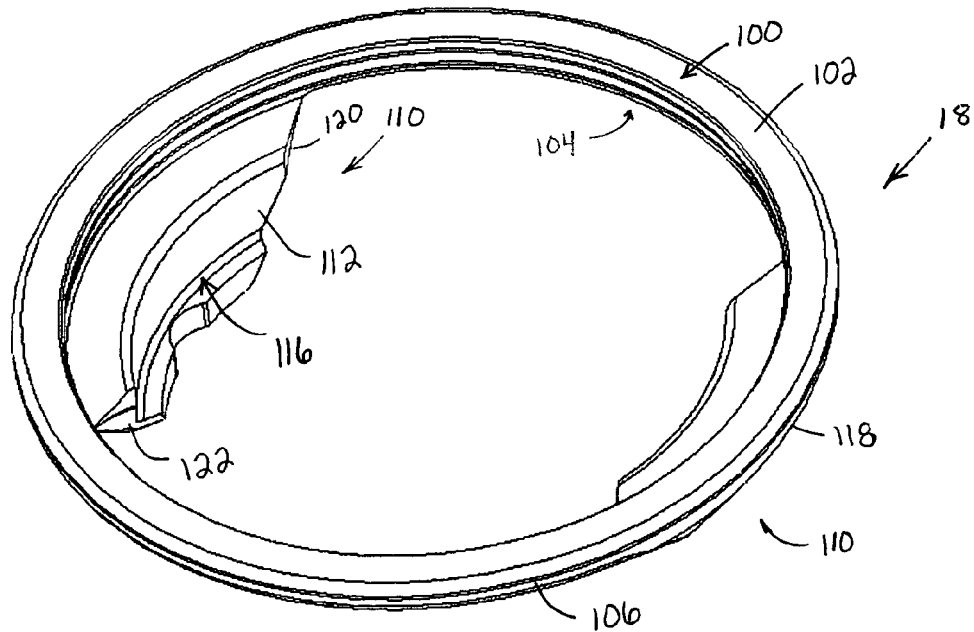
FIG. 6 is another perspective view of the constraining component of FIG. 1.

Turning now to FIGS. 1, 5, and 6, an exemplary constraining component 18 has a circular or ring-shape body portion 100. Body 100 has a flat or planar bottom surface 102 that smoothly transitions to a top surface 104. Preferably, body 100 has a round transition or round edge 106 that forms an outer surface between bottom surface 102 and top surface 104.

Two extensions 110 extend outwardly from body portion 100. Preferably, these extensions are oppositely disposed. Extensions 110 have a body with an inner wall or surface 112 and an outer wall or surface 114. Both surfaces circumferentially extend around a portion of circular ring body 100. Surface 112 has a step or terrace 116 that extends along the length of surface 112. This step 116 is shaped and sized to engage and mate with step 66 formed on wall 64 of extensions 54. Surface 114 has a smooth surface with a spherical or conical contour. Surface 114 makes a smooth and rounded edge 118 along the transition between surface 114 and bottom surface 102. Two gaps or cutouts 119 are formed between extensions 110. These cutouts are oppositely disposed from each other.

In the exemplary embodiment, body 100 includes two end surfaces 120 and 122 that taper inwardly toward each other.

Surface 114 makes a smooth and rounded edge 119 along the transition between surface 114 and end surfaces 120 and 122. These end surfaces have smooth rounded corners and are preferably not perpendicular with top surface 104. Instead, surfaces 120 and 122 form an obtuse angle Φ with surface 104. These surfaces 120 and 122 thus taper or slope inwardly from surface 104 to a top surface 126. Preferably, the taper on these surfaces is constant, gradual, and symmetric with respect to each other. Further, angle Φ is equal to angle θ. Further, in the exemplary embodiment, the extensions are similarly shaped but may be formed with different sizes. For example, one extension may be larger than the other. Alternatively, the extensions can have the same size.

Figure 7:
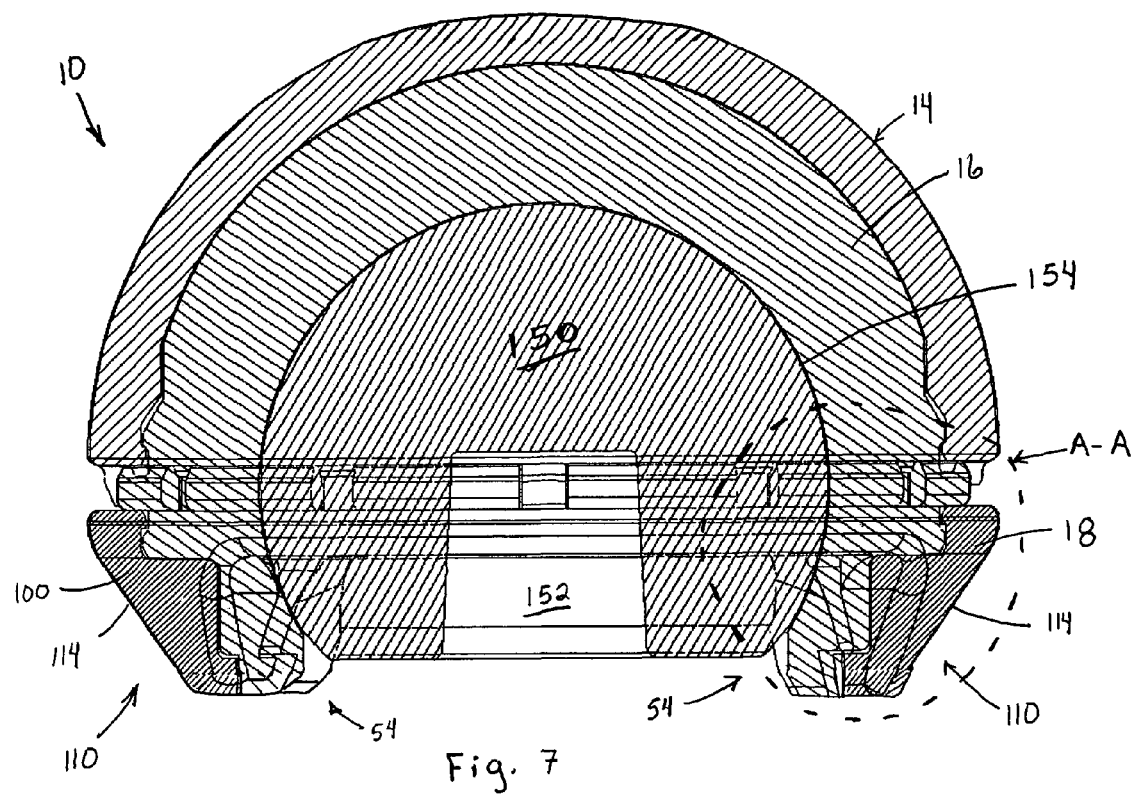
FIG. 7 is a cross-sectional type view of an assembled acetabular component and acetabular shell with a femoral ball.
Figure 8:
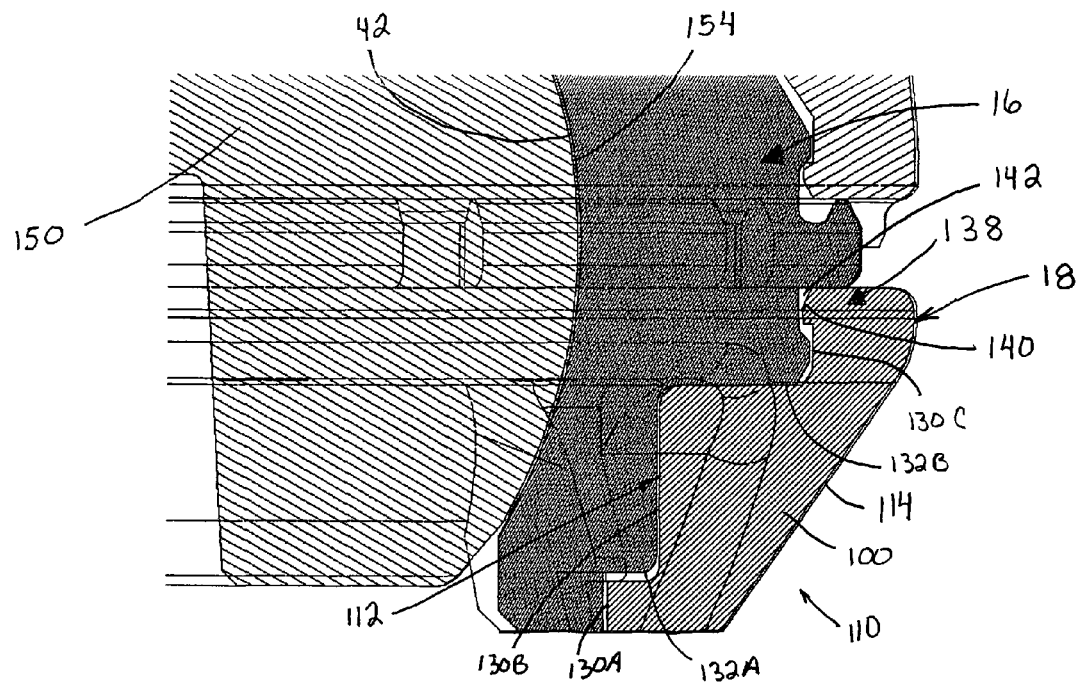
FIG. 8 is an enlarged view taken along circular lines A—A of FIG. 7.

Looking also to FIGS. 7 and 8, extensions 110 have a generally triangular cross section. Outer surfaces 114 taper or slope inwardly toward the center of ring-shaped body 100. Inner surface 112 is formed of three different vertical surfaces 130A–130C and two horizontal surfaces 132A and 132B. Together, these surfaces form the stepped or terrace configuration that engages the stepped configuration on the outer surface of extensions 54.

As best shown in FIG. 8, a locking mechanism 138 connects the constraining component 18 to the articulating component 16. Body 100 may include a shoulder 140 that extends inwardly toward a center of the body. This shoulder is adapted to engage in a corresponding channel or recess 142 formed along the outer surface of articulating component 16. The shoulder 140 and recess 142 can be sized and shaped to form a snapping or locking engagement to lock and hold the constraining component 18 to the articulating component 16.

The locking mechanism can have various configurations to perform the function of locking the constraining component to the articulating component. This locking mechanism can be adapted to permanently connect the constraining component to the articulating component or removeably connect these two components so the constraining component can be attached, detached, and re-attached to the articulating component.

As seen in FIGS. 7 and 8, a femoral ball 150 has a tapered recess 152 adapted to receive a neck of the femoral hip stem. The ball 150 is positioned in the cavity of the articulating component so an outer surface 154 of the ball can smoothly articulate with the inner surface 42 of the articulating component. As the ball is positioned into the cavity of the articulating component, extensions 54 radially flex outwardly to accommodate the diameter of the ball. Once the ball is positioned in the cavity, the extensions resiliently flex back to their original position and capture the ball within the cavity. The constraining component 18 is engaged and locked to the articulating component as shown in FIGS. 7 and 8. In this position, the constraining component prohibits the extensions 54 from radially flexing outwardly. As such, the ball is lockingly captured or retained within the cavity of the articulating component.

In order to remove the femoral ball from the cavity of the articulating component, constraining component 18 is disengaged and removed from articulating component 16. As the ball is removed from the cavity of the articulating component, extensions 54 radially flex outwardly to accommodate the diameter of the ball. Once the ball is removed, the extensions resiliently flex back to their original position.

During range of motion of the femoral hip stem, the neck and body of the stem will not impinge against the body of the constraining or articulating components until extreme angles of range of motion are experienced. The stem can move between the cutouts of both the constraining and articulating components.

The acetabular component may be made from different biocompatible materials. The articulating component, for example, can be formed from highly cross-linked UHMWPE; and the constraining component can be formed from high strength materials, such as titanium, cobalt chrome alloy, stainless steel, etc.

In the exemplary embodiment, the constraining and articulating components each included two cutouts or recesses and two extensions. Alternatively, both of these components can employ a single cutout and a single extension. Further, multiple extensions and cutouts can be utilized. Further, the cutouts and extensions can be similarly configured or differently configured. Further yet, cutouts and extensions can be positioned in different circumferential orientations about the constraining and articulating components. For example, they can be oppositely disposed, spaced adjacent each other, or spaced in other circumferential orientations.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. An acetabular prosthesis, comprising:
an acetabular shell;
an acetabular articulating component having a partial spherical shape with an inner surface forming a partial spherical cavity adapted to receive a femoral ball, the articulating component being connectable to the shell; and
an acetabular constraining component connectable to the articulating component and having a ring shape body with two extensions extending outwardly from the body, the extensions having a triangular cross section, wherein said acetabular articulating component further comprises a plurality of extensions, each of which comprise a stepped outer surface, and wherein each of said extensions of said acetabular constraining component further comprise:
an outer surface that slopes inwardly toward a center of the body;
two end walls that are sloped and form an obtuse angle with the body; and
a stepped inner surface comprised of three vertical surfaces and two horizontal surfaces that defines a stepped configuration on said inner surface, said stepped inner surface being adapted to mate with said stepped outer surface.

2. The acetabular prosthesis of claim 1 wherein the extensions have an outer surface that slopes inwardly toward a center of the body.

3. The acetabular prosthesis of claim 2 wherein the outer surface has a rounded edge.

4. The acetabular prosthesis of claim 3 wherein the extensions have two end walls that are sloped and form an obtuse angle with the body.

5. The acetabular prosthesis of claim 1 wherein the ring shape body has a shoulder that extends inwardly toward a center of the body; the shoulder being adapted to engage and lock with an outer surface of the articulating component.

6. The acetabular prosthesis of claim 1 wherein the extensions have an inner surface that includes at least one step.

7. The acetabular prosthesis of claim 6 wherein the step is adapted to seat against the articulating component.

8. An acetabular component, comprising:
an acetabular articulating component having a spherical shape and an inner surface forming at least a partial spherical cavity adapted to receive a femoral ball; and
an acetabular constraining component connected to the articulating component for locking the femoral ball within the spherical cavity, the constraining component having a circular body and two extensions and two cutouts, wherein the extensions project outwardly from the body and inwardly toward a center of the body, wherein said acetabular articulating component further comprises a plurality of extensions, each of which comprise a stepped outer surface, and wherein each of said extensions of said acetabular constraining component further comprise:
an outer surface that slopes inwardly toward a center of the body;
two end walls that are sloped and form an obtuse angle with the body; and
a stepped inner surface comprised of three vertical surfaces and two horizontal surfaces that defines a stepped configuration on said inner surface, said stepped inner surface being adapted to mate with said stepped outer surface.

9. The acetabular component of claim 8 wherein each extension has an outer surface that slopes inwardly toward the center.

10. The acetabular component of claim 9 wherein each extension has two end surfaces that are sloped and form an obtuse angle with the circular body.

11. The acetabular component of claim 10 wherein each extension has an inner surface oppositely disposed from the outer surface, the inner surface including at least one terrace.

12. The acetabular component of claim 11 wherein the cutouts are oppositely disposed and the extensions are oppositely disposed.

13. The acetabular component of claim 8 wherein each extension has a triangular cross sectional shape.

14. The acetabular component of claim 8 further including a locking mechanism that snappingly connects the constraining component to the articulating component.

15. The acetabular component of claim 14 wherein the locking mechanism includes a shoulder that engages a recess.

16. An acetabular prosthesis adapted to replace a portion of a natural acetabulum, the prosthesis comprising:
an acetabular shell;
an acetabular insert connectable to the shell and having an inner surface that forms a partial spherical cavity to articulate with a femoral ball; and
a constraining component connectable to the insert, the constraining component having a circular body portion with at least one extension extending outwardly from the body portion, wherein the extension has an outer surface that extends inwardly toward a center of the circular body portion, wherein said acetabular articulating component further comprises a plurality of extensions, each of which comprise a stepped outer surface, and wherein each of said extensions of said acetabular constraining component further comprise:
an outer surface that slopes inwardly toward a center of the body;
two end walls that are sloped and form an obtuse angle with the body; and
a stepped inner surface comprised of three vertical surfaces and two horizontal surfaces that defines a stepped configuration on said inner surface, said stepped inner surface being adapted to mate with said stepped outer surface.

17. The acetabular prosthesis of claim 16 wherein the extension has at least one rounded edge.

18. The acetabular prosthesis of claim 17 wherein the insert includes a base portion with at least one extension extending downwardly from the base portion, and the extension on the constraining component includes a stepped inner surface adapted to engage the extension on the insert.

19. The acetabular prosthesis of claim 18 wherein the extension on the constraining component includes a stepped surface.

20. The acetabular prosthesis of claim 16 wherein the extension has two end surfaces that taper inwardly toward each other.

* * * * *